United States Patent
Vanderpohl, III

(10) Patent No.: US 9,177,465 B2
(45) Date of Patent: Nov. 3, 2015

(54) BED STATUS SYSTEM FOR A PATIENT SUPPORT APPARATUS

(71) Applicant: Hill-Rom Services, Inc., Batesville, IN (US)

(72) Inventor: Irvin J. Vanderpohl, III, Greensburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 48 days.

(21) Appl. No.: 14/136,214

(22) Filed: Dec. 20, 2013

(65) Prior Publication Data

US 2014/0184409 A1 Jul. 3, 2014

Related U.S. Application Data

(60) Provisional application No. 61/746,742, filed on Dec. 28, 2012.

(51) Int. Cl.
| | |
|---|---|
| *G08B 1/08* | (2006.01) |
| *G08B 25/01* | (2006.01) |
| *G06F 19/00* | (2011.01) |
| *A61G 7/05* | (2006.01) |
| *G08B 21/22* | (2006.01) |

(52) U.S. Cl.
CPC ............. *G08B 25/016* (2013.01); *A61G 7/05* (2013.01); *G06F 19/327* (2013.01); *G08B 21/22* (2013.01)

(58) Field of Classification Search
CPC ............... G06F 19/3418; G06Q 10/063114; A61B 5/1113; G08B 25/00; G08B 21/22

USPC .............. 340/539.22, 573.1, 286.01, 286.07, 340/539.12, 591.6, 13.24; 705/2
See application file for complete search history.

(56) References Cited

U.S. PATENT DOCUMENTS

| | | | |
|---|---|---|---|
| 3,991,414 A | 11/1976 | Moran | |
| 4,135,241 A | 1/1979 | Stanis et al. | |
| 4,261,109 A | 4/1981 | Mikus et al. | |
| 5,561,412 A | 10/1996 | Novak et al. | |
| 5,699,038 A | 12/1997 | Ulrich et al. | |
| 5,715,548 A | 2/1998 | Weismiller et al. | |
| 5,771,511 A | 6/1998 | Kummer et al. | |
| 5,838,223 A * | 11/1998 | Gallant et al. | 340/286.07 |
| 6,147,592 A * | 11/2000 | Ulrich et al. | 340/286.07 |
| 6,163,903 A | 12/2000 | Weismiller et al. | |
| 6,208,250 B1 | 3/2001 | Dixon et al. | |
| 6,279,183 B1 | 8/2001 | Kummer et al. | |
| 6,320,510 B2 | 11/2001 | Menkedick et al. | |
| 6,336,235 B1 | 1/2002 | Ruehl | |
| 6,362,725 B1 | 3/2002 | Ulrich et al. | |
| 6,566,833 B2 | 5/2003 | Bartlett | |
| 6,611,979 B2 | 9/2003 | Welling et al. | |
| 6,658,680 B2 | 12/2003 | Osborne et al. | |

(Continued)

OTHER PUBLICATIONS

European Search Report for EP 13199451.9-1952 dated Feb. 18, 2014, 6 pages.

(Continued)

*Primary Examiner* — Phung Nguyen
(74) *Attorney, Agent, or Firm* — Barnes & Thornburg LLP

(57) ABSTRACT

A bed status system includes a patient support apparatus having a status, a location unit configured to provide a location to the patient support apparatus, and a bed status module coupled to the location unit and the patient support apparatus to receive the status and the location.

20 Claims, 10 Drawing Sheets

(56) References Cited

U.S. PATENT DOCUMENTS

| | | |
|---|---|---|
| 6,691,346 B2 | 2/2004 | Osborne et al. |
| 6,791,460 B2 | 9/2004 | Dixon et al. |
| 6,876,303 B2 | 4/2005 | Reeder et al. |
| 6,880,189 B2 | 4/2005 | Welling et al. |
| 6,897,780 B2 | 5/2005 | Ulrich et al. |
| 6,957,461 B2 | 10/2005 | Osborne et al. |
| 6,978,500 B2 | 12/2005 | Osborne et al. |
| 6,988,012 B2 | 1/2006 | Renz |
| 7,017,208 B2 | 3/2006 | Weismiller et al. |
| 7,017,211 B2 | 3/2006 | Krywiczanin et al. |
| 7,092,376 B2 | 8/2006 | Schuman |
| 7,126,467 B2 | 10/2006 | Albert et al. |
| 7,129,833 B2 | 10/2006 | Albert |
| 7,148,797 B2 | 12/2006 | Albert |
| 7,154,397 B2 | 12/2006 | Zerhusen et al. |
| 7,170,404 B2 | 1/2007 | Albert et al. |
| 7,171,708 B2 | 2/2007 | Osborne et al. |
| 7,173,525 B2 | 2/2007 | Albert |
| 7,213,279 B2 | 5/2007 | Weismiller et al. |
| 7,237,287 B2 | 7/2007 | Weismiller et al. |
| 7,242,308 B2 | 7/2007 | Ulrich et al. |
| 7,315,535 B2 | 1/2008 | Schuman |
| 7,319,386 B2 | 1/2008 | Collins, Jr. et al. |
| 7,343,302 B2 | 3/2008 | Aratow et al. |
| 7,391,316 B2 | 6/2008 | Albert et al. |
| 7,403,110 B2 | 7/2008 | Albert et al. |
| 7,443,302 B2 | 10/2008 | Reeder et al. |
| 7,454,805 B2 | 11/2008 | Osborne et al. |
| 7,472,440 B2 | 1/2009 | Bartlett et al. |
| 7,477,143 B2 | 1/2009 | Albert |
| 7,477,144 B2 | 1/2009 | Albert |
| 7,480,951 B2 | 1/2009 | Weismiller et al. |
| 7,508,307 B2 | 3/2009 | Albert |
| 7,522,035 B2 | 4/2009 | Albert |
| 7,538,659 B2 | 5/2009 | Ulrich et al. |
| 7,568,246 B2 | 8/2009 | Weismiller et al. |
| 7,629,890 B2 | 12/2009 | Sullivan et al. |
| 7,654,948 B2 | 2/2010 | Kaplan et al. |
| 7,656,287 B2 | 2/2010 | Albert et al. |
| 7,679,520 B2 | 3/2010 | Zerhusen et al. |
| 7,690,059 B2 | 4/2010 | Lemire et al. |
| 7,715,387 B2 | 5/2010 | Schuman |
| 7,746,218 B2 | 6/2010 | Collins, Jr. et al. |
| 7,784,128 B2 | 8/2010 | Kramer |
| 7,805,784 B2 | 10/2010 | Lemire et al. |
| 7,813,941 B2 | 10/2010 | Auker et al. |
| 7,831,447 B2 | 11/2010 | Schuman |
| 7,834,768 B2 | 11/2010 | Dixon et al. |
| 7,852,208 B2 | 12/2010 | Collins, Jr. et al. |
| 7,861,334 B2 | 1/2011 | Lemire et al. |
| 7,868,740 B2 | 1/2011 | McNeely et al. |
| 7,911,349 B2 | 3/2011 | Zerhusen et al. |
| 7,962,981 B2 | 6/2011 | Lemire et al. |
| 7,971,300 B2 | 7/2011 | Wilker, Jr. |
| 7,978,084 B2 | 7/2011 | Dixon et al. |
| 7,986,242 B2 | 7/2011 | Dixon et al. |
| 7,996,935 B1 | 8/2011 | Chen |
| 8,000,977 B2 | 8/2011 | Achan |
| 8,026,821 B2 | 9/2011 | Reeder et al. |
| 8,031,057 B2 | 10/2011 | McNeely et al. |
| 8,046,625 B2 | 10/2011 | Ferguson et al. |
| 8,065,764 B2 | 11/2011 | Kramer |
| 8,082,160 B2 | 12/2011 | Collings, Jr. et al. |
| RE43,193 E | 2/2012 | Osborne et al. |
| 8,120,471 B2 | 2/2012 | Collins, Jr. et al. |
| 8,121,856 B2 | 2/2012 | Huster et al. |
| 8,151,387 B2 | 4/2012 | Osborne et al. |
| 8,169,304 B2 | 5/2012 | Schuman, Sr. et al. |
| 8,219,416 B2 | 7/2012 | Auker et al. |
| 8,258,963 B2 | 9/2012 | Dixon et al. |
| 8,258,965 B2 | 9/2012 | Reeder et al. |
| 8,266,742 B2 | 9/2012 | Andreienko |
| 8,280,748 B2 | 10/2012 | Allen et al. |
| 8,284,047 B2 | 10/2012 | Collins, Jr. et al. |
| 8,314,781 B2 | 11/2012 | Pittenger et al. |
| 8,334,777 B2 | 12/2012 | Wilson et al. |
| 8,334,779 B2 | 12/2012 | Zerhusen et al. |
| 8,344,860 B2 | 1/2013 | Collins, Jr. et al. |
| 8,368,545 B2 | 2/2013 | Zerhusen et al. |
| 8,384,526 B2 | 2/2013 | Schuman, Sr. et al. |
| 8,392,747 B2 | 3/2013 | Ferguson et al. |
| 8,393,026 B2 | 3/2013 | Dionne et al. |
| 8,400,311 B2 | 3/2013 | Dixon et al. |
| 8,413,274 B2 | 4/2013 | Weismiller et al. |
| 8,421,606 B2 | 4/2013 | Collins, Jr. et al. |
| 8,432,287 B2 | 4/2013 | O'Keefe et al. |
| 8,456,286 B2 | 6/2013 | Schuman et al. |
| 8,461,968 B2 | 6/2013 | Ball et al. |
| 8,487,774 B2 | 7/2013 | Reeder et al. |
| 8,512,221 B2 | 8/2013 | Kaplan et al. |
| 8,525,680 B2 | 9/2013 | Riley et al. |
| 8,525,682 B2 | 9/2013 | Dixon et al. |
| 8,536,990 B2 | 9/2013 | Collins, Jr. et al. |
| 8,537,008 B2 | 9/2013 | Tallent et al. |
| 8,544,126 B2 | 10/2013 | Elliott et al. |
| 8,560,580 B1 | 10/2013 | Nacey |
| 8,571,884 B2 | 10/2013 | Badgett et al. |
| 8,572,778 B2 | 11/2013 | Newkirk et al. |
| 8,593,284 B2 | 11/2013 | Tallent et al. |
| 8,598,995 B2 | 12/2013 | Schuman et al. |
| 8,604,916 B2 | 12/2013 | McNeely et al. |
| 8,604,917 B2 | 12/2013 | Collins et al. |
| 8,612,252 B1 | 12/2013 | Gravins |
| 8,634,981 B1 | 1/2014 | Hyde et al. |
| 8,674,839 B2 | 3/2014 | Zerhusen et al. |
| 8,799,011 B2 * | 8/2014 | Wilson et al. ............ 705/2 |
| 2009/0212925 A1 * | 8/2009 | Schuman et al. ...... 340/286.07 |

OTHER PUBLICATIONS

Statement in Accordance with the Notice From the European Patent Office Dated Oct. 1, 2007 Concerning Business Methods—EPC/ Nov. 1, 2007, XP007905525, 1 page.

Notice from the European Patent Office dated Oct. 1, 2007 concerning business methods, Nov. 1, 2007, pp. 592-593, XP007905525, 2 pages.

* cited by examiner

BED STATUS SYSTEM FOR A PATIENT SUPPORT APPARATUS

CROSS-REFERENCE TO RELATED APPLICATIONS

The present application claims the benefit, under 35 U.S.C. §119(e), of U.S. Provisional Application No. 61/746,742, which was filed Dec. 28, 2012, and which is hereby incorporated by reference herein in its entirety.

BACKGROUND

The present disclosure relates to a patient support apparatus, and in particular, to a patient support apparatus configured to communicate a status of the patient support apparatus to a remote output. More particularly, the present disclosure relates to a bed status system configured to receive a location of the patient support apparatus and a status of the patient support apparatus and communicate the status to the remote output.

Patient support apparatuses may be configured to determine a status of various pieces of equipment included in the patient support apparatus. Status information may include a height of a patient support surface above ground, position of siderails included in the patient support apparatus, inflation state of an inflatable air mattress included in the patient support apparatus, whether a patient has attempted to or exited the patient support apparatus, and other similar statuses. Once statuses are known, the patient support apparatus may communicate locally the statuses to an area in a patient room in which the patient support apparatus is also located.

Caregivers desiring to determine the status of equipment included in the patient support apparatus must enter physically each room to receive the status communication provided by each patient support apparatus. As a result, caregivers must spend significant time and resources to obtain the status of each patient support apparatus in each patient room in a healthcare facility.

SUMMARY

This application discloses one or more of the features recited in the appended claims and/or the following features which, alone or in any combination, may comprise patentable subject matter.

In one aspect of the present disclosure, a bed status system includes a location unit, a patient support apparatus, and a bed status module. The location unit is located in a patient room and is configured to provide location data associated with the patient room to a predetermined area in the patient room. The patient support apparatus is adapted to support a patient thereon and configured to receive the location data from the location unit when the patient support apparatus is located in the patient room in the predetermined area. The patient support apparatus is further configured to provide the location data and apparatus data associated with a status of the patient support apparatus. The bed status module is arranged to lie outside the patient room and is configured to receive the location data and the apparatus data to cause information to be provided to a caregiver that communicates the location and status of the patient support apparatus without the caregiver entering the patient room.

In some embodiments, the patient support apparatus may include a patient support structure, a patient support surface, and a control system. The patient support surface may be coupled to the patient support structure to move between a raised position and a lowered position. The control system may be coupled to the patient support structure to cause the patient support surface to move. The control system may provide a patient support structure status included in the apparatus data that indicates whether the patient support structure is in one of the raised position and the lowered position.

In some embodiments, the patient support surface may include an inflatable air mattress coupled to the patient support structure to move therewith. The inflatable air mattress may be coupled to the controller to change between a first inflation state in which air pressure is maintained at a first pressure and a second inflation state in which air pressure is minimized to cause stress imparted to the patient to be minimized without causing the patient to contact the patient support deck. The control system may be configured to provide a surface status included in the apparatus data that indicates whether the inflatable air mattress is in one of the first inflation state and the second inflation state.

In some embodiments, the control system may be configured to provide a bed-exit status included in the apparatus data. The bed-exit status may indicate whether a bed-exit event has occurred.

In some embodiments, the patient support structure may include a lower frame, an upper frame, and a siderail. The upper frame may be movable relative to the lower frame. The siderail may be coupled to the upper frame to move between a raised position in which a portion of the siderail extends above patient support surface and a lowered position in which the siderail lies below the patient support surface. The control system may be configured to provide a siderail status included in the apparatus data that indicates whether the siderail is in one of the raised position and the lowered position.

In some embodiments, the information provided by the bed status module may include a separate indicator that is associated with each of the patient support structure status, the surface status, the bed-exist status, and the siderail status. Each indicator may change from a first state to a second state in response to a change in the status associated with each indicator. Each indicator may be a visual indicator. Each indicator may be an audio indicator.

In some embodiments, the information provided by the bed status module may include an indicator that changes from a first state to a second state in response to a change in the status of the patient support apparatus. The indicator may be a visual indicator or an audio indicator.

In some embodiments, the location unit may provide the location data via a first wireless signal. The patient support apparatus may be configured to receive the location data by the first wireless signal and the patient support apparatus provides the location data and the apparatus data via a second wireless signal. The bed status module may be configured to receive the second wireless signal.

In some embodiments, bed status system may further comprise a remote server. The remote server may be configured to lie in spaced-apart relation to the patient room. The remote server may be configured to receive the location data and apparatus data provided by the patient support apparatus and communicate the location data and apparatus data to the bed status module.

In another aspect of the present disclosure, a bed status system comprises a location unit and a bed status module. The location unit may be located in a patient room and configured to provide location data wirelessly to a predetermined area in the patient room. The bed status module may be arranged to lie outside the patient room and configured to receive the location data and apparatus data associated with a status of a patient support apparatus when the patient support apparatus is located in the predetermined area of the patient room. The bed status module may be configured to provide information to a caregiver that communicates the location and status of the patient support apparatus without the caregiver being located in the patient room.

In some embodiments, the location unit may receive the apparatus data from the patient support apparatus. The location unit may send the location data and the apparatus to the bed status module.

In some embodiments, the bed status system may further comprise a second location unit located in spaced-apart relation to the location unit in the patient room. The second location unit may be configured to provide second location data wirelessly to a second predetermined area in the patient room. The second predetermined area may be spaced apart from the first predetermined area. The bed status module may be configured to receive the location data and the second location data and second apparatus data associated with a status of a second patient support apparatus when the second patient support apparatus is located in the second predetermined area of the patient room.

In some embodiments, the bed status module may include a user interface. The user interface may be configured to provide the information to the caregiver. The user interface may be configured to receive a user input to cause the information provided by the bed status module to change in response to receiving the user input. The user input may be a delay input that causes the information provided by the bed status module to change in response to receiving the delay input for a predetermined period of time.

Additional features alone or in combination with any other feature(s), including those listed above, those listed in the claims, and those described in detail below, may comprise patentable subject matter. Other features will become apparent to those skilled in the art upon consideration of the following detailed description of illustrative embodiments exemplifying the best mode of carrying out the invention as presently perceived.

BRIEF DESCRIPTIONS OF THE DRAWINGS

The detailed description particularly refers to the accompanying figures in which.

DETAILED DESCRIPTION

Figure 1:
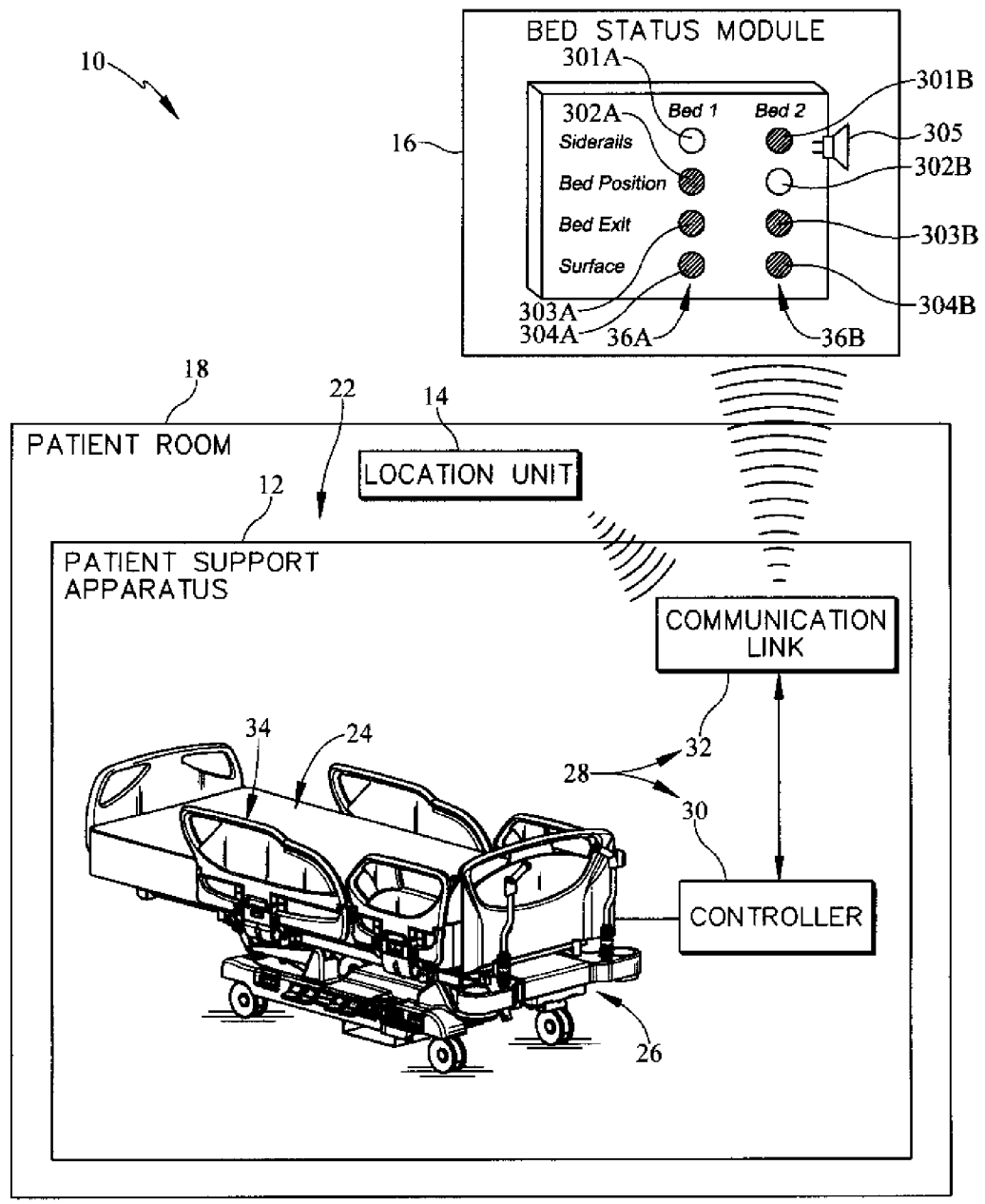
FIG. 1 is diagrammatic view of a first embodiment of a bed status system in accordance with the present disclosure.
Figure 2:
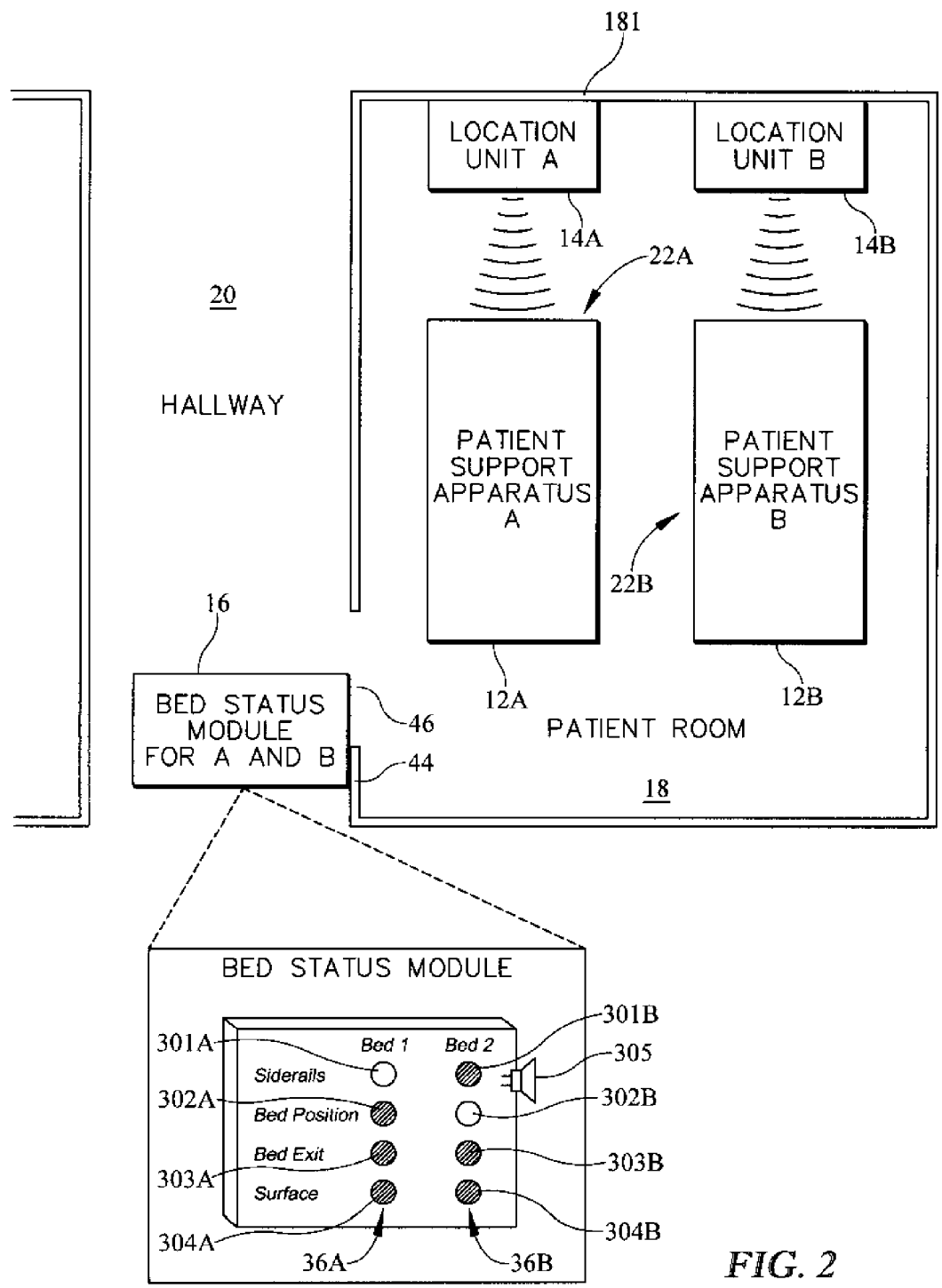
FIG. 2 is a diagrammatic view of the bed status system of FIG. 1 showing that the bed status system communicates a status of each patient support apparatus located in a patient room to a caregiver outside the patient room.

A bed status system 10 in accordance with the present disclosure includes a patient support apparatus 12, a location unit 14, and a bed status module 16 as shown in FIGS. 1 and 2. The patient support apparatus 12 is located, for example, in a patient room 18 of a healthcare facility. The location unit 14 is coupled to a wall 181 of the patient room and configured to transmit a location of the location unit 14 to a predetermined area 22 of the patient room 18. The bed status module 16 is located outside the patient room 18 and is configured to receive the location of the patient support apparatus 12 when the patient support apparatus 12 is located in the predetermined area 22 of the patient room 18. The bed status module 16 is also configured to receive information from the patient support apparatus 12 that is indicative of a status of various pieces of equipment and processes included in the patient support apparatus as shown in FIGS. 1 and 2.

The bed status system 10 is configured to provide a caregiver located outside a patient room 18 with information associated with a status of equipment and processes included in the patient support apparatus 12 without the caregiver entering the patient room 18 as suggested in FIG. 2. In one illustrative example, a caregiver in a facility may look down a hallway 20 in the facility and receive information from multiple bed status modules 16 located in the hallway 20 as suggested in FIG. 2. The caregiver is then able to determine the status of all equipment and processes included in all the patient support apparatuses on the hallway 20. As a result, the caregiver may only visit those patient rooms with issues identified by the bed status system 10, and thus, minimize time and resources wasted entering each patient room to check on the status of each patient support apparatus located in the patient room.

As shown in FIG. 1, the patient support apparatus 12 includes a patient support surface 24, a patient support structure 26, and a control system 28. The patient support structure 26 rests on ground underlying the patient support surface and is movable relative to the ground. The patient support surface 24 is coupled to the patient support structure 26 and is adapted to support the patient resting on the patient support apparatus 12. Control system 28 is coupled to both the patient support structure 26 and the patient support surface 24 to control movement of the patient support structure 26 relative to ground, configuration of the patient support surface 24, communicate with external components, and determine statuses of equipment and processes include in the patient support apparatus 12.

Illustratively, the control system 28 includes a controller 30, a communication link 32, and a sensor as suggested in FIG. 1. Communication link 32 is configured to receive signals from the location unit 14 and transmit those signals to the controller 30 for processing. For example, the location unit 14 is coupled to a headwall of the patient room 18 and transmits location data to the predetermined area 22 of the patient room 18 as shown in FIG. 2. When the patient support apparatus 12 is located in the predetermined area 22, the communication link 32 receives the location data and transmits the location data to the controller 30.

Controller 30 is configured to receive information from equipment, processes, and sensors included in the patient support apparatus 12. Equipment may include an inflatable mattress included in the patient support surface 24, an actuator included in the patient support structure 26, a braking device included in the patient support structure, and any other suitable pieces of equipment. Processes may include a process for detecting bed exit, a process for providing a microclimate to the patient support surface, a process for monitoring patient movement, and any other suitable process. Sensors may include a head angle sensor that determine an angle of the patient's back and head relative to ground, a wetness sensor that detects an incontinence event, and any other suitable sensors which may be coupled to the patient or the patient support apparatus.

Controller 30 receives the data from the equipment, processes, and equipment and then determines a status of the equipment, processes, and sensors included in the patient support apparatus 12. Controller 30 communicates this apparatus data including the various statues to the bed status module 16 by way of the communication link 32. Controller 30 also sends location data from the location unit 14 to the bed status module 16. Bed status module 16 then combines the apparatus data and location data to cause information to be provided to caregiver that communicates the location and the status of the patient support apparatus 12 as suggested in FIG. 1.

Figure 8:
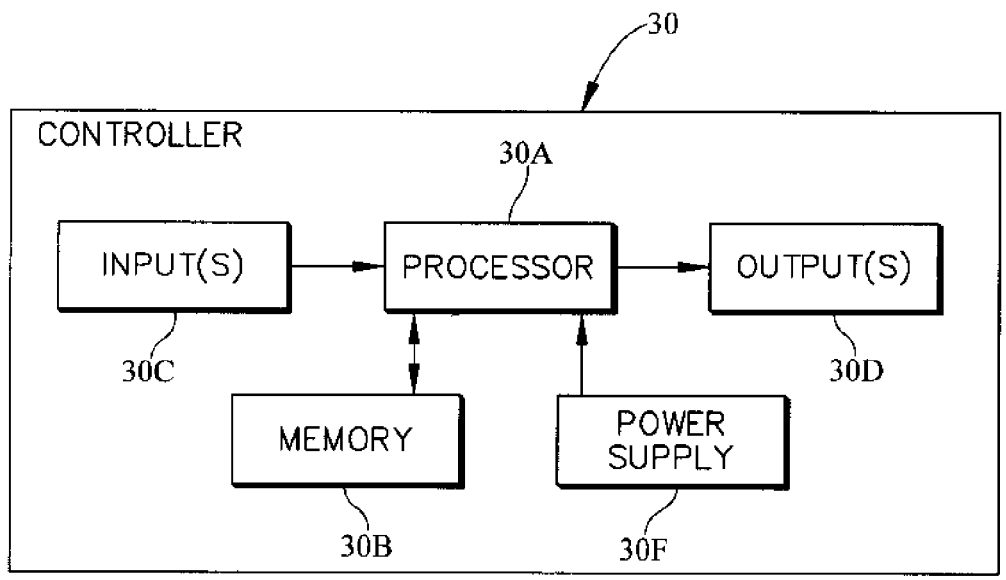
FIG. 8 is a diagrammatic view of one embodiment of a controller in accordance with the present disclosure.

The controller 30 includes a processor 30A, memory 30B, one or more inputs 30C, and one or more outputs 30D as shown in FIG. 8. Status information may be received by processor 30A via inputs 30C and stored in memory 30B. In addition, processor 30A may execute various processes such as a bed exit alarm process which monitors various inputs to determine if the bed exit alarm should activated. Once the processor 30A makes such a determination, the processor 30A sends commands via outputs 30D to cause an alarm to sound or a visual indicator to be displayed. In another example, a sensor may be one of the inputs 30C. Outputs 30D of controller 30 may be couple to actuators, blowers, etc. to control various equipment and processes included in the patient support apparatus. The processor 30A may store information received from inputs 30C for additional processing, collection of additional data, or communication via communication link 32.

In another example, the controller 30 may further include a power supply 30F as shown in FIG. 8. The power supply 30F may be a battery which supplies power to the processor 30A. The power supply 30F may also be a wire which is coupled to a power supply included in the patient support apparatus. The power supply 30F may also include a transformer which provides power from the patient support apparatus or an electrical wall socket to the processor 516A at an appropriate voltage and frequency.

Figure 7:
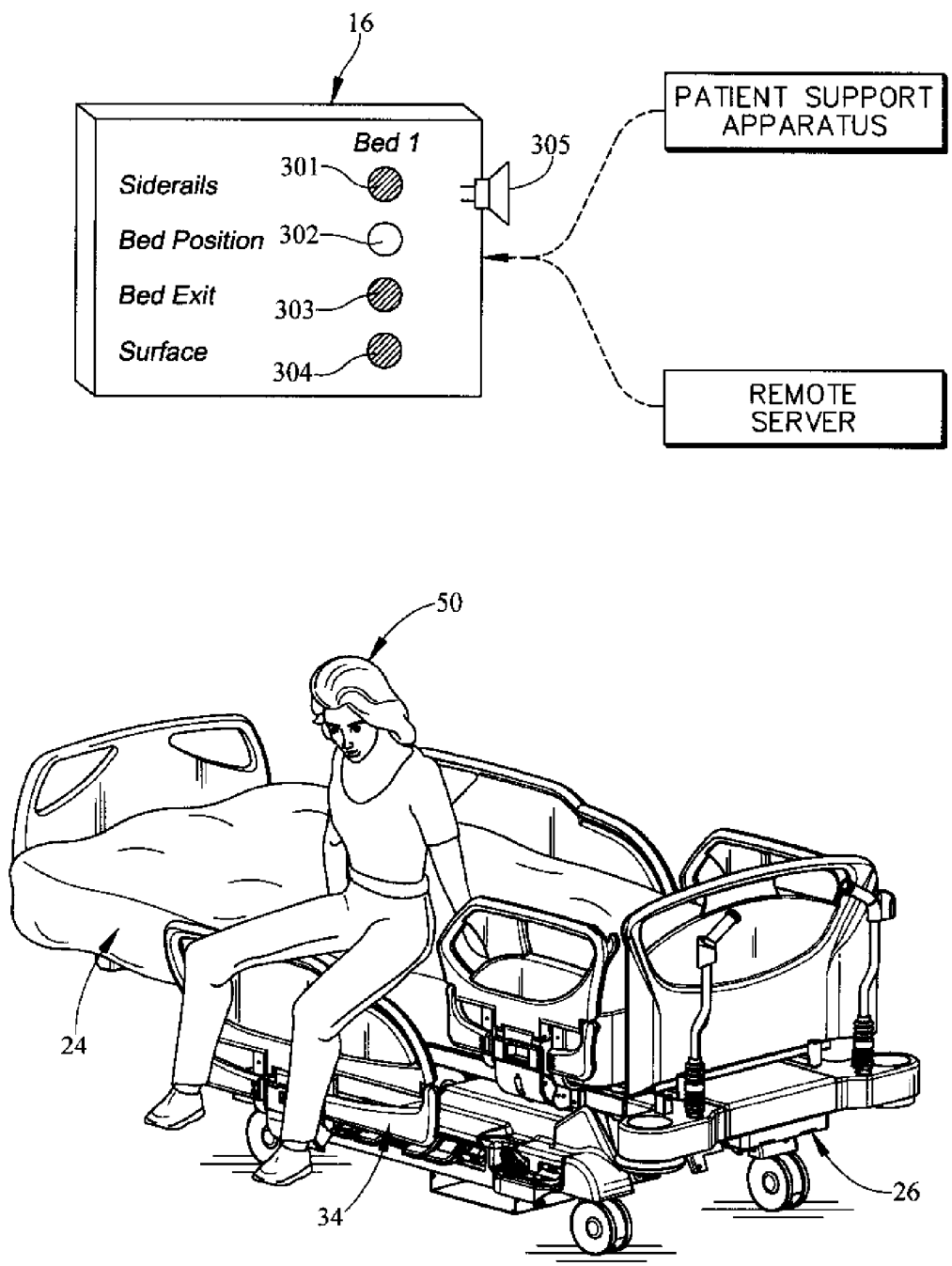
FIG. 7 is a diagrammatic and perspective view of a fourth embodiment of a bed status system in accordance with the present disclosure showing the bed status system in an example of use.

In one example of use, a patient 50 has lowered a siderail 34 included in the patient support apparatus 12 and is attempting to egress from the patient support apparatus 12 as shown in FIG. 7. In addition, the patient has configured the patient support surface 24 to be firm increasing chances for the development of pressure ulcer formation on the patient 50. At the same time, the patient support structure 26 has been lowered previously to its lowest position by a caregiver to minimize damage to the patient 50 from a fall should the patient 50 attempt to exit the patient support apparatus 12. Controller 30 provides apparatus data which includes a siderail position, a surface configuration, bed-exit alarms, and a patient support structure position.

In the example shown in FIG. 7, the controller 30 communicates the apparatus data by way of the communication link 32 to the bed status module 16 which in turn causes visual indicators 301, 302, 303, 304 associated with each piece of equipment to change to the appropriate visual indicator for the status. In the illustrative example of FIG. 7, bed status module 16 causes a first visual indicator 301 associated with the siderails to change from green, indicating a desired status, to red, indication an undesired status as a result of the siderail 34 being in a lowered position. The bed status module 16 also causes a second visual indicator 302 to remain green as the patient support structure 26 is in the lowered position. Bed status module 16 causes a third visual indicator 303 associated with a bed-exit alarm to change from green to red as controller 30 had determined the patient 50 is attempting to exit the patient support apparatus 12. Finally, the bed status module 16 causes a fourth visual indicator 304 associated with the patient support surface 24 to change from green to red because the patient support surface 24 is in a firm configuration.

In the illustrative examples of FIGS. 1-5 and 7, the controller 30 provides apparatus information which includes a status for siderail position, patient support structure position, bed exit alarm, and patient support surface status. However, the status of other equipment included in the patient support apparatus 12 may also be included in the apparatus information. Such status information may include, an angle of a patient's back and head relative to the patient support structure, the occurrence of an incontinence event, environment conditions such as temperature and humidity between the patient and the patient support surface, failure of a patient to move during a predetermined time period, equipment failure on the patient support apparatus, and any other suitable events, equipment, or processes.

The bed status module 16 may also include an audio output 305 which may sound if one ore more of the statuses are in an undesirable state as shown in FIGS. 1 and 7. The audio output may be the same when any status becomes undesirable or specific patterns of sound may be emitted when various combinations of status are undesirable.

The location unit 14 is configured to transmit location data to the predetermined area 22 in the patient room 18. In one illustrative example, the location unit 14 transmits the location data wirelessly. Wireless transmission may be achieved by emitting an infrared beam, sending a wireless signal over an 802.11 local area network, sending a wireless signal via BLUETOOTH® technology, or any other suitable alternative.

The communication link 32 included in the patient support apparatus 12 is configured to receive location data from the location unit 14 and send both location data and apparatus data to the bed status module 16 or other device. The communication link 32 may be configured to receive an infrared beam, a wireless signal over an 802.11 local area network, a wireless signal via BLUETOOTH® technology, or any other suitable alternative from the location unit 14. The communication link 32 may also be configured to send apparatus to the bed status module wireless via a wireless signal over an 802.11 local area network, a wireless signal via BLUETOOTH® technology, or any other suitable alternative.

As shown, for example, in FIG. 2, the bed status module 16 may be provide information associated with one or more patient support apparatuses included in a patient room. As shown in FIG. 2, a first patient support apparatus 12A is located in the patient room 18. A second patient support apparatus 12B is located in spaced-apart relation to the first patient support apparatus 16A in the patient room 18. A first location unit 14A is mounted on a wall 181 of the patient room 18 and is configured to send location data to a first predetermined area 22A in the patient room 18. A second location unit 14B is mounted in spaced-apart relation on the wall 181 of the patient room and is configured to send location data to a second predetermined area 22B in the patient room. Both patient support apparatuses 12A, 12B receive location data from their associated location units 14A, 14B and then communicate associated apparatus data and location data to the bed status module 16 which is located in the hallway 20.

The bed status module 16 may be configured to show a first set 36A of visual indicators associated with the status of the first patient support apparatus 12A when the first patient support apparatus 12A is in the first predetermined area 22A. The first set 36A of visual indicators may include first, second, third, and fourth visual indicators 301A, 302A, 303A, 304A associated with various equipment and programs included in the first patient support apparatus 12A. The bed status module 16 may also show a second set 36B of visual indicators associated with the status of the second patient support apparatus 12B when the second patient support apparatus 12B is in the second predetermined area 22B. The second set 36B of visual indicators may include first, second, third, and fourth visual indicators 301B, 302B, 303B, 304B associated with various equipment and programs included in the second patient support apparatus 12B.

While only one patient room 18 is shown on the hallway 20, multiple patient rooms may be located on the hallway 20. As a result, multiple bed status modules may be located in the hallway 20 that each associated with one patient room. As a result, there may be a one-to-one relationship between bed status modules and patient rooms. However, there may also be a one-to-many relationship between bed status modules and patient rooms. In one example, a first bed status module associated with one patient room may be located in the hallway 20. A second bed status module associated with all the patient rooms on the hallway may be located at a nurse station, break room, or other suitable location.

Figure 3:
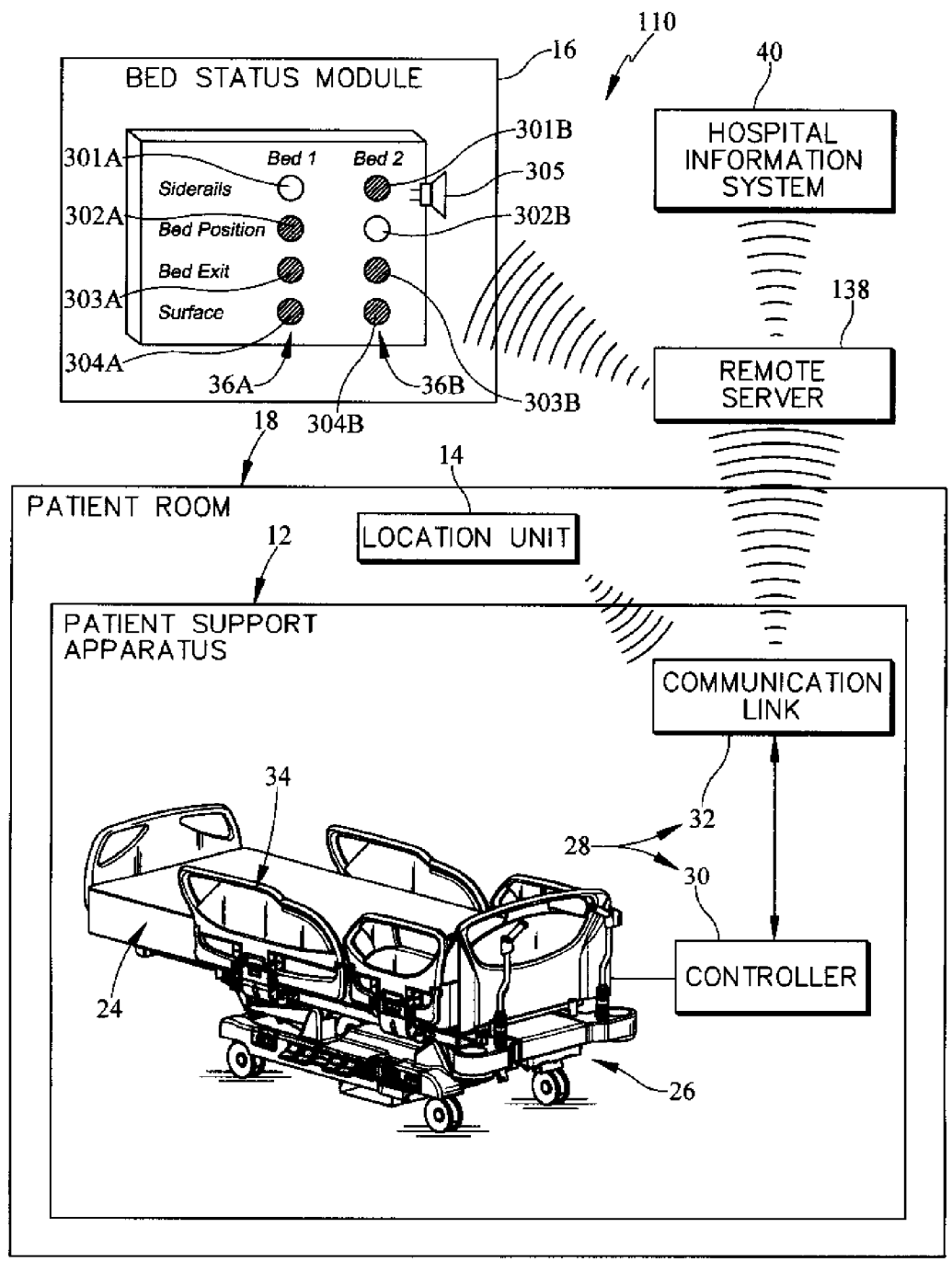
FIG. 3 is a diagrammatic view of a second embodiment of a bed status system in accordance with the present disclosure.

Another embodiment of a bed status system 110 in accordance with the present disclosure is shown, for example, in FIG. 3. The bed status system 110 includes the patient support apparatus 12, the location unit 14, the bed status module 16, and a remote server 138. The controller 30 included in the patient support apparatus 12 receives location data from the location unit 14 and determines apparatus data from the patient support apparatus 12. The controller 30 then communicates the location and apparatus data to the communication link 32 which sends the data to the remote server 138 as shown in FIG. 3.

The remote server 138 may process the location data and the apparatus data and provide specific signals to the bed status module 16. In this example, the bed status module only includes relays which cause the sets 36A, 36B of visual indicators to change to the proper status. The remote server 138 may also store the location and apparatus data for future review and auditing. As shown in FIG. 3, the remote server 138 may also send the location and apparatus data to a hospital information system 40 where the data may be archived or entered into an electronic medical record associated with the patient.

Figure 4:
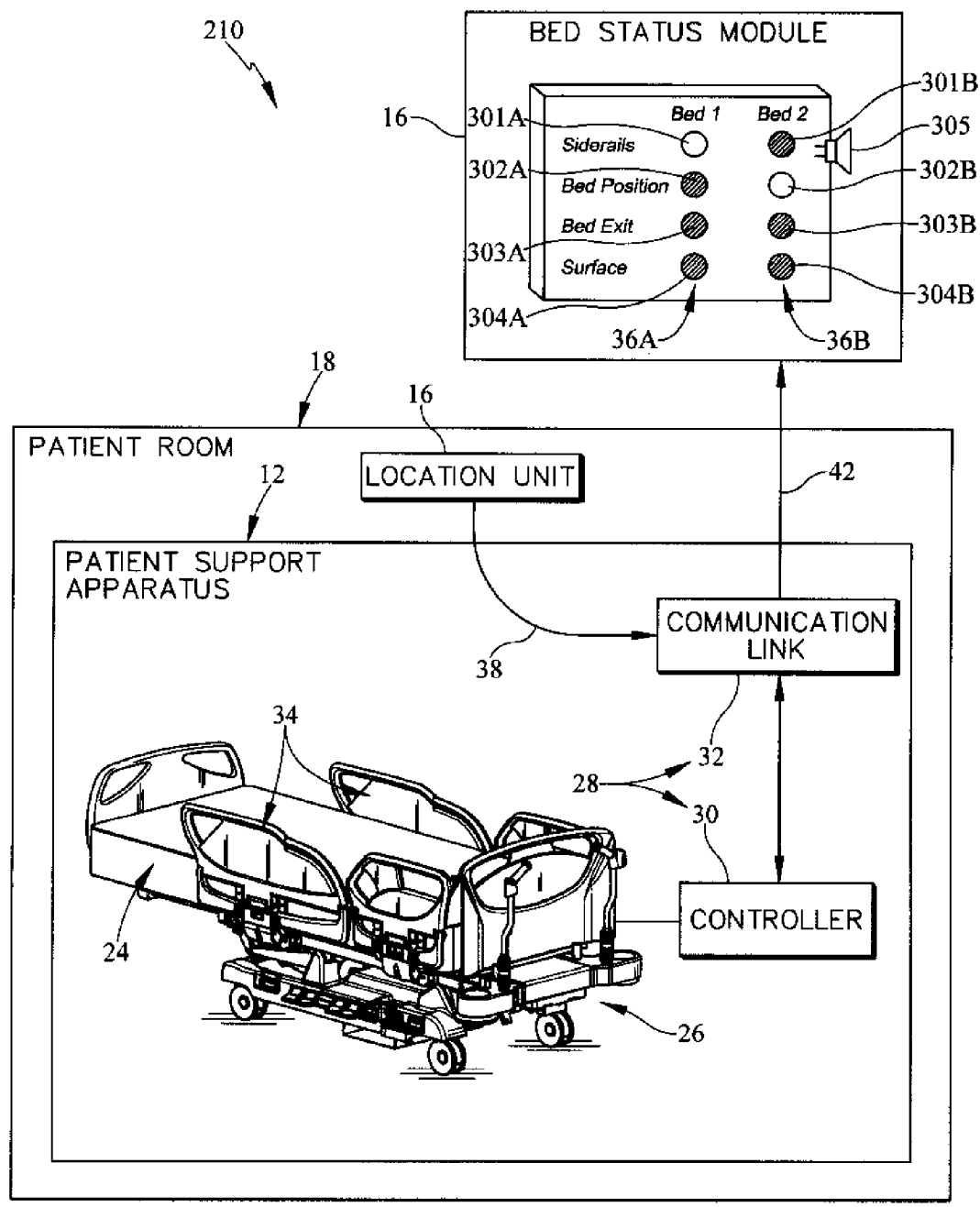
FIG. 4 is a diagrammatic view of a third embodiment of a bed status system in accordance with the present disclosure.

Another embodiment of a bed status system 210 in accordance with the present disclosure is shown, for example, in FIG. 4. The bed status system 210 includes the patient support apparatus 12, the location unit 14, and the bed status module 16. The controller 30 included in the patient support apparatus 12 receives location data from the location unit 14 via a wire 38 and determines apparatus data from the patient support apparatus 12. The controller 30 then communicates the location and apparatus data to the communication link 32 which sends the data to the remote server 138 via another wire 42 as shown in FIG. 4. While the location unit 14 and the communication link 32 may be configured for wireless communication, they may also be configured to communicate across wired connections as shown in FIG. 4.

Figure 5:
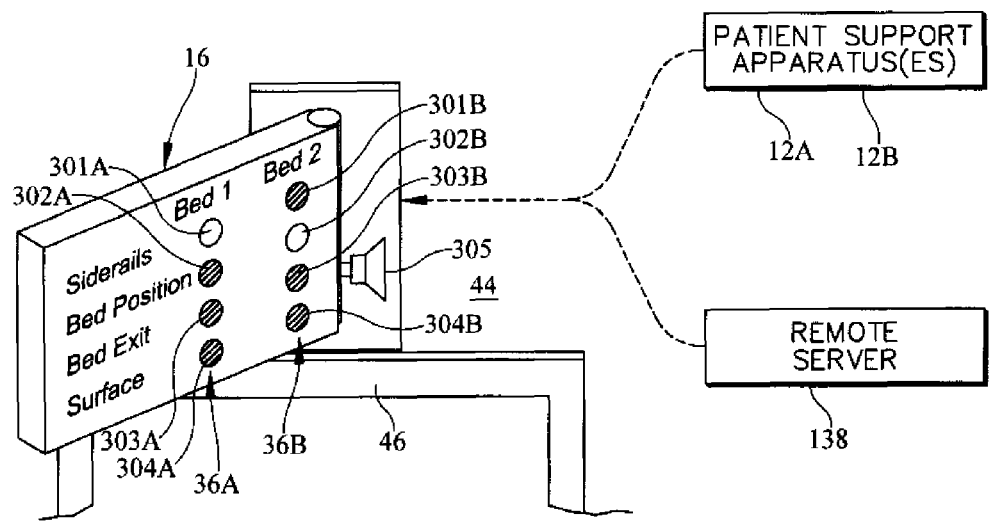
FIG. 5 is a diagrammatic and perspective view of a first embodiment of a bed status module located above a patient-room doorway in a hallway.

A first embodiment of the bed status module 16 is shown for example in FIG. 5. The bed status module 16 may be located in the hallway 20 and coupled to a wall 44 above a doorway 46 that leads to the patient room 18. The bed status module 16 may be configured to communicate information about each patient support apparatus located in the patient room 18 to caregivers located outside the patient room 18. As shown in FIG. 5, the bed status module 16 includes the first set 36A of visual indicators 301A, 302A, 303A, 304A associated with the first patient support apparatus 12A. The bed status module 16 further includes the second set 36B of visual indicators 301B, 302B, 303B, 304B associated with the second patient support apparatus 12B. The bed status module 16 also includes the audio output 305. The bed status module 16 may be used with any combination of bed status systems 10, 110, and 210.

Figure 6:
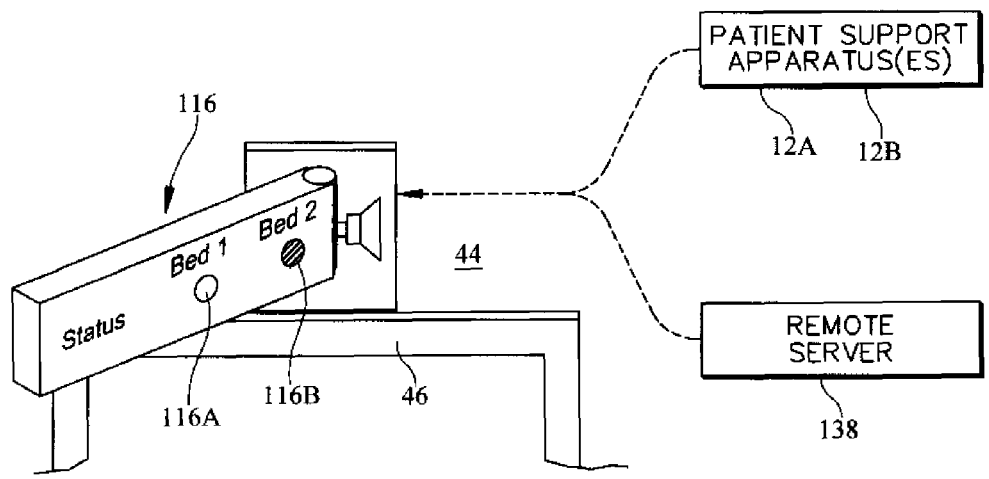
FIG. 6 is a diagrammatic and perspective view of a second embodiment of a bed status module located above the patient-room doorway in the hallway.

Another embodiment of a bed status module 116 is shown in FIG. 6. The bed status module 116 is located in the hallway 20 and coupled to the wall 44 above the doorway 46 that leads to the patient room 18. The bed status module 16 is configured to communicate information about each patient support apparatus located in the patient room 18 to caregivers located outside the patient room 18. Unlike the bed status module 16, this bed status module 116 only provides an overall visual indicator for each patient support apparatus. As shown in FIG. 6, the first patient support apparatus 12A has a green visual indicator 116A which means the status of all equipment and processes included in the first patient support apparatus are in a desirable state. However, the second patient support apparatus 12B has a red visual indicator 116B which means that at least one of the pieces of equipment or processes in the patient support apparatus have an undesirable status. As a result, the overall visual indicator 116B for the second patient support apparatus is red. The bed status module 116 may also include the audio output 305. The bed status module 116 may be used with any combination of bed status systems 10, 110, and 210.

Figure 9:
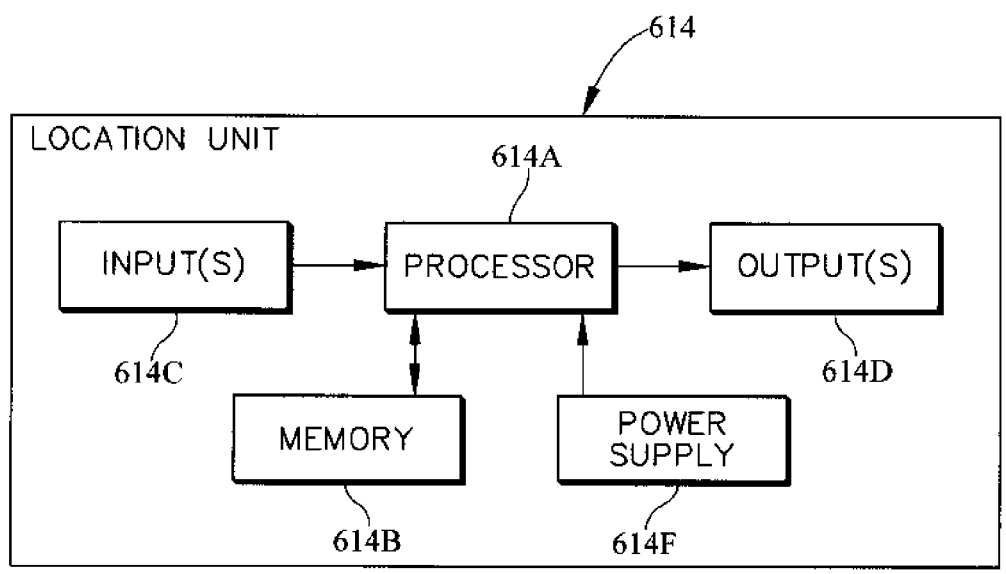
FIG. 9 is a diagrammatic view of one embodiment of a location unit in accordance with the present disclosure.

One embodiment of a location unit 614 is shown, for example, in FIG. 9. The location unit 614 is known as a smart location unit 614 as a result of the location unit 614 including a processor 614A, memory 614B, one or more inputs 614C, and one or more outputs 614D as shown in FIG. 9. The apparatus data may be communicated to the processor 614A of the location unit 614 via one of the inputs 614C. The location unit 614 may communicate the location data via one of the outputs 614D to the bed status module or the patient support apparatus. The location data may be stored on the memory 614B along with instructions for sending the location data to the predetermined area 22. These instructions may include location, frequency, and information to be provided in the location data. However, the location unit may also be a dumb location unit in which no processing occurs other than the communication of location data and relay of apparatus data.

In another example, the location unit 614 may further include a power supply 614F as shown in FIG. 9. The power supply 614F may be a battery which supplies power to the processor 614A. The power supply 614F may also be a transformer and a power cord which provides power from an electrical wall socket to the transformer which provides power to the processor 614A at an appropriate voltage and frequency.

Figure 11:
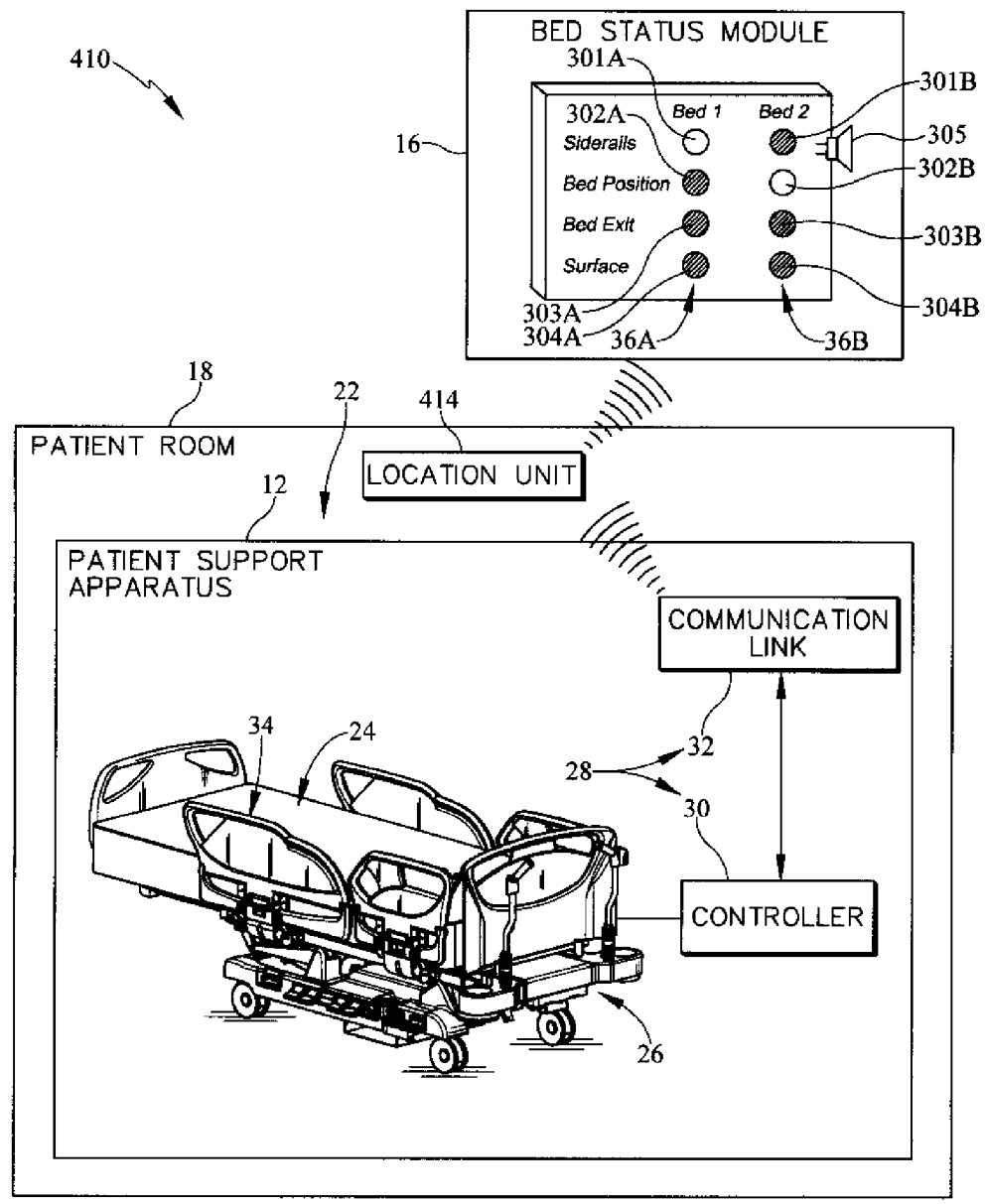
FIG. 11 is a diagrammatic view of a fifth embodiment of a bed status system in accordance with the present disclosure.

Another embodiment of a bed status system 410 in accordance with the present disclosure is shown, for example, in FIG. 11. The bed status system 410 includes the patient support apparatus 12, a location unit 414, and the bed status module 16. The controller 30 included in the patient support apparatus 12 provides apparatus data to the location unit 414. The controller 30 communicates wirelessly with the location unit 414 via the communication link 32 as shown in FIG. 11. The location unit 414 receives the apparatus data and provides both the apparatus data and location data to the bed status module 414. As shown in FIG. 11, the location unit 414 may communicate with the bed status module wirelessly. While the location unit 14 and the communication link 32 may be configured for wireless communication, they may also be configured to communicate across wired connections as suggested in FIG. 4.

Figure 12:
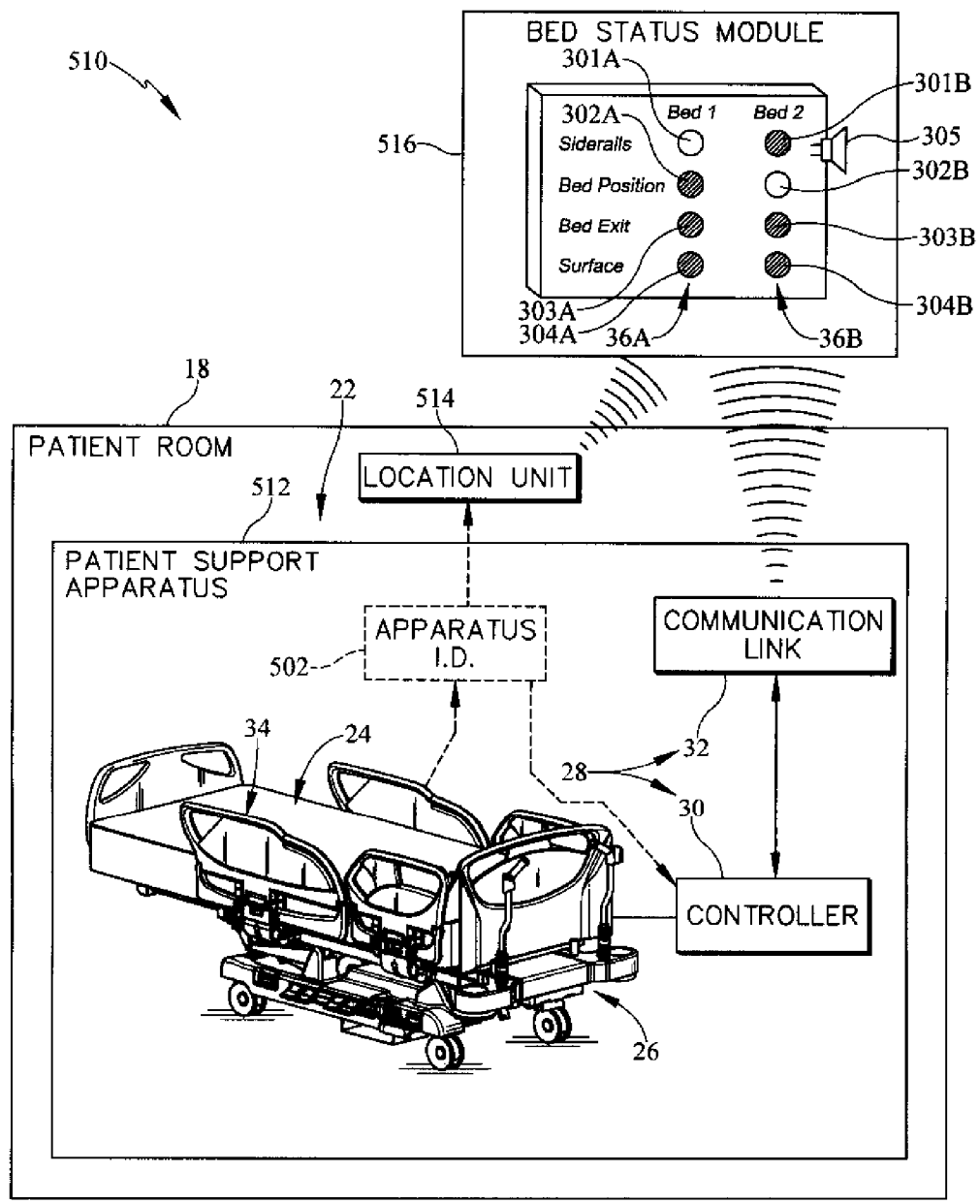
FIG. 12 is a diagrammatic view of a sixth embodiment of a bed status system in accordance with the present disclosure.

Still yet another embodiment of a bed status system 510 in accordance with the present disclosure is shown, for example, in FIG. 12. The bed status system 510 includes the patient support apparatus 512, a location unit 514, and the bed status module 516. The patient support apparatus 512 is configured to provide apparatus data that includes status of various pieces of equipment and processes in the patient support apparatus 512 and an apparatus ID 502 which includes information which identifies the patient support apparatus. The controller 30 included in the patient support apparatus 512 provides apparatus data, including the apparatus ID 502, to the bed status system 510. The location unit 514 receives the apparatus ID 502 from the patient support apparatus 512 when the patient support apparatus 512 is in the predetermined area 22. The location unit 514 then communicates the location data and the apparatus ID 502 to the bed status module 516 as suggested in FIG. 12.

Figure 10:
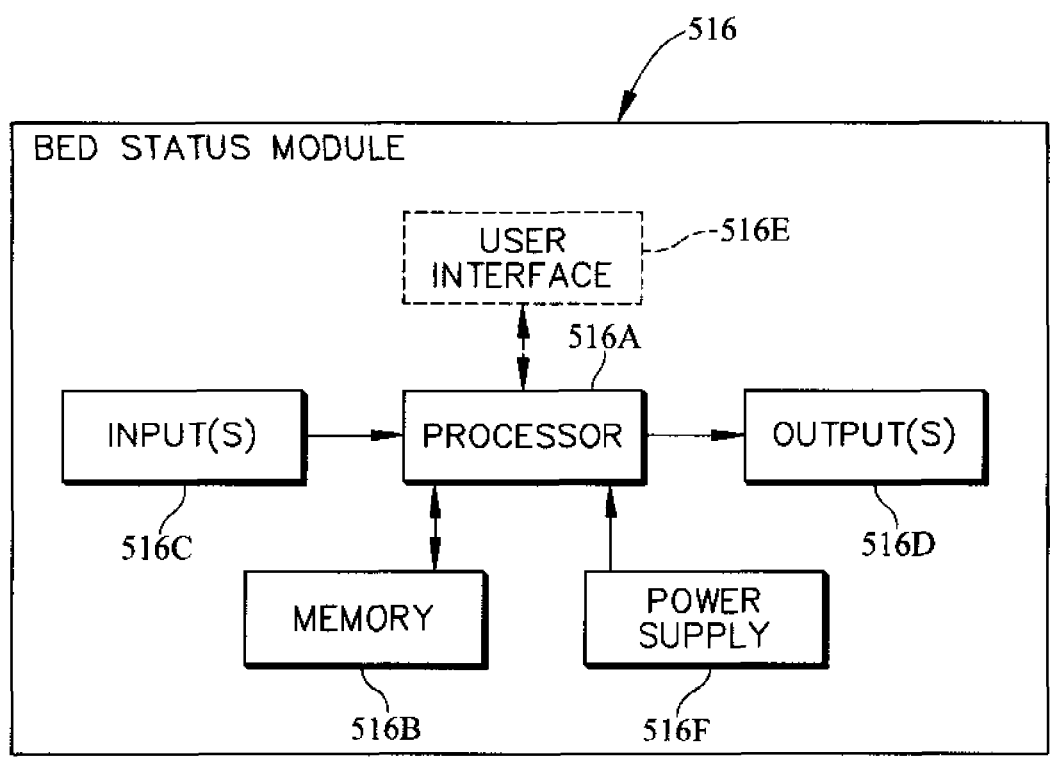
FIG. 10 is a diagrammatic view of one embodiment of a bed status module in accordance with the present disclosure.

The bed status module 516 receives the apparatus data, the location data, and the apparatus ID 502 from the patient support apparatus 512 and the location unit 514 as shown in FIG. 12. The bed status module then combines the apparatus ID 502 received with the location data with the apparatus ID 502 received with the apparatus data and to cause the appropriate visual indicators to be displayed as suggested in FIG. 14. The bed status module 516 is known as a smart bed status module as a result of the bed status module 516 including a processor 516A, memory 516B, one or more inputs 516C, and one or more outputs 516D as shown in FIG. 10. The apparatus data and the location data may be received via inputs 516C, processed by the processor 516A, and stored in the memory 516B. The processor 516A, when receiving apparatus data, may look up which visual indicators should be displayed in a table stored in the memory 516B. The processor 516A then sends commands via one or more outputs 516D that causes the appropriate visual indicators to be displayed.

As shown in FIG. 10, the bed status module 516 may also include a user interface 516E which is coupled to the processor 516A. The user interface 516E may be configured to display the visual indicators suggested in FIGS. 1-7, 11, and 12. The user interface 516 may also be configured to receive user input and communicate the user input back to the processor 516A. The user interface may, in one illustrative example, be a touch screen interface which both provides visual output but also receives user input.

In one illustrative example, the user interface may display that the bed egress alarm has been tripped. The caregiver may provide a delay input to the user interface 516E of the bed status module 516 that causes the visual indicator associated with the bed egress alarm to be reset, put on hold for a predetermined period of time, or forwarded to another caregiver. However, the bed status module may also be a dumb bed status module in which no processing occurs other than the providing the appropriate visual indicator in response to receiving the location and apparatus data.

In another example, the bed status module 516 may further include a power supply 516F as shown in FIG. 10. The power supply 516F may be a battery which supplies power to the processor 516A. The power supply 516F may also be a transformer and a power cord which provides power from an electrical wall socket to the transformer which provides power to the processor 516A at an appropriate voltage and frequency.

The invention claimed is:

1. A bed status system comprising
a location unit located in a patient room and configured to provide location data associated with the patient room to a predetermined area in the patient room,
a patient support apparatus adapted to support a patient thereon and configured to receive the location data from the location unit when the patient support apparatus is located in the patient room in the predetermined area, the patient support apparatus being further configured to provide the location data and apparatus data associated with a status of the patient support apparatus, and
a bed status module arranged to lie outside the patient room and configured to receive the location data and the apparatus data to cause information to be provided to a caregiver that communicates the location and status of the patient support apparatus without the caregiver entering the patient room,
wherein the patient support apparatus includes a patient support structure, a patient support surface coupled to the patient support structure to move between a raised position and a lowered position, and a control system coupled to the patient support structure to cause the patient support surface to move and to provide a patient support structure status included in the apparatus data that indicates whether the patient support structure is in one of the raised position and the lowered position, and
wherein the patient support surface includes an inflatable air mattress coupled to the patient support structure to move therewith, the inflatable air mattress is coupled to the controller to change between a first inflation state in which air pressure is maintained at a first pressure and a second inflation state in which air pressure is minimized to cause stress imparted to the patient to be minimized without causing the patient to contact the patient support deck, and the control system is configured to provide a surface status included in the apparatus data that indicates whether the inflatable air mattress is in one of the first inflation state and the second inflation state.

2. The bed status system of claim 1, wherein the control system is configured to provide a bed-exit status included in the apparatus data that indicates whether a bed-exit event has occurred.

3. The bed status system of claim 2, wherein the patient support structure includes a lower frame, an upper frame movable relative to the lower frame, and a siderail coupled to the upper frame to move between a raised position in which a portion of the siderail extends above patient support surface and a lowered position in which the siderail lies below the patient support surface and the control system is configured to provide a siderail status included in the apparatus data that indicates whether the siderail is in one of the raised position and the lowered position.

4. The bed status system of claim 3, wherein the information provided by the bed status module includes a separate indicator that is associated with each of the patient support structure status, the surface status, the bed-exist status, and the siderail status and each indicator changes from a first state to a second state in response to a change in the status associated with each indicator.

5. The bed status system of claim 4, wherein each indicator is a visual indicator.

6. The bed status system of claim 4, wherein each indicator is an audio indicator.

7. The bed status system of claim 3, wherein the information provided by the bed status module includes an indicator that changes from a first state to a second state in response to a change in the status of the patient support apparatus.

8. The bed status system of claim 7, wherein the indicator is a visual indicator.

9. The bed status system of claim 7, wherein the indicator is an audio indicator.

10. The bed status system of claim 1, wherein the information provided by the bed status module includes an indicator that changes from a first state to a second state in response to a change in the status of the patient support apparatus.

11. A bed status system comprising
a location unit located in a patient room and configured to provide location data associated with the patient room to a predetermined area in the patient room,
a patient support apparatus adapted to support a patient thereon and configured to receive the location data from the location unit when the patient support apparatus is located in the patient room in the predetermined area, the patient support apparatus being further configured to provide the location data and apparatus data associated with a status of the patient support apparatus, and
a bed status module arranged to lie outside the patient room and configured to receive the location data and the apparatus data to cause information to be provided to a caregiver that communicates the location and status of the patient support apparatus without the caregiver entering the patient room,
wherein the location unit provides the location data via a first wireless signal, and
wherein the patient support apparatus is configured to receive the location data by the first wireless signal and the patient support apparatus provides the location data and the apparatus data via a second wireless signal.

12. The bed status system of claim 11, wherein the bed status module is configured to receive the second wireless signal.

13. The bed status system of claim 11, further comprising a remote server configured to lie in spaced-apart relation to the patient room and to receive the location data and apparatus data provided by the patient support apparatus and communicate the location data and apparatus data to the bed status module.

14. The bed status system of claim 11, wherein the information provided by the bed status module includes an indicator that changes from a first state to a second state in response to a change in the status of the patient support apparatus.

15. A bed status system comprising
a location unit located in a patient room and configured to provide location data wirelessly to a predetermined area in the patient room and
a bed status module arranged to lie outside the patient room and configured to receive the location data and apparatus data associated with a status of a patient support apparatus when the patient support apparatus is located in the predetermined area of the patient room, the bed status module is configured to provide information to a caregiver that communicates the location and status of the patient support apparatus without the caregiver being located in the patient room,
wherein the location unit receives the apparatus data from the patient support apparatus and sends the location data and the apparatus to the bed status module.

16. The bed status system of claim 15, wherein the information provided by the bed status module includes an indicator that changes from a first state to a second state in response to a change in the status of the patient support apparatus.

17. A bed status system comprising
a location unit located in a patient room and configured to provide location data wirelessly to a predetermined area in the patient room and
a bed status module arranged to lie outside the patient room and configured to receive the location data and apparatus data associated with a status of a patient support apparatus when the patient support apparatus is located in the predetermined area of the patient room, the bed status module is configured to provide information to a caregiver that communicates the location and status of the patient support apparatus without the caregiver being located in the patient room,
a second location unit located in spaced-apart relation to the location unit in the patient room and configured to provide second location data wirelessly to a second predetermined area in the patient room, the second predetermined area being spaced apart from the first predetermined area and the bed status module being configured to receive the location data and the second location data and second apparatus data associated with a status of a second patient support apparatus when the second patient support apparatus is located in the second predetermined area of the patient room.

18. The bed status system of claim 17, wherein the information provided by the bed status module includes an indicator that changes from a first state to a second state in response to a change in the status of the patient support apparatus.

19. A bed status system comprising
a location unit located in a patient room and configured to provide location data wirelessly to a predetermined area in the patient room and
a bed status module arranged to lie outside the patient room and configured to receive the location data and apparatus data associated with a status of a patient support apparatus when the patient support apparatus is located in the predetermined area of the patient room, the bed status module is configured to provide information to a caregiver that communicates the location and status of the patient support apparatus without the caregiver being located in the patient room,
wherein the bed status module includes a user interface configured to provide the information to the caregiver and configured to receive a user input to cause the information provided by the bed status module to change in response to receiving the user input, and
wherein the user input is a delay input that causes the information provided by the bed status module to change in response to receiving the delay input for a predetermined period of time.

20. The bed status system of claim 19, wherein the information provided by the bed status module includes an indicator that changes from a first state to a second state in response to a change in the status of the patient support apparatus.

\* \* \* \* \*